(12) United States Patent
Miyasaka et al.

(10) Patent No.: US 12,123,885 B2
(45) Date of Patent: Oct. 22, 2024

(54) SAMPLE DISCRIMINATION SYSTEM AND SAMPLE AUTOMATIC PROCESSING APPARATUS USING SAME, AND SAMPLE DISCRIMINATION METHOD

(71) Applicant: HITACHI HIGH-TECH CORPORATION, Tokyo (JP)

(72) Inventors: Tooru Miyasaka, Tokyo (JP); Toru Shibata, Tokyo (JP); Katsuhiro Kambara, Tokyo (JP); Shigeki Yamaguchi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 826 days.

(21) Appl. No.: 17/272,702

(22) PCT Filed: Oct. 11, 2019

(86) PCT No.: PCT/JP2019/040206
§ 371 (c)(1),
(2) Date: Mar. 2, 2021

(87) PCT Pub. No.: WO2020/085121
PCT Pub. Date: Apr. 30, 2020

(65) Prior Publication Data
US 2021/0373041 A1  Dec. 2, 2021

(30) Foreign Application Priority Data
Oct. 25, 2018 (JP) ................. 2018-201034

(51) Int. Cl.
*G01N 35/00* (2006.01)
*G01N 35/02* (2006.01)

(52) U.S. Cl.
CPC ....... *G01N 35/00722* (2013.01); *G01N 35/02* (2013.01); *G01N 2035/0091* (2013.01)

(58) Field of Classification Search
None
See application file for complete search history.

(56) References Cited

U.S. PATENT DOCUMENTS

| 8,992,832 B2* | 3/2015 | Donnerbauer | ..... G01N 21/6408 |
| | | | 250/483.1 |
| 10,241,048 B2* | 3/2019 | Izuka | ..... G01N 33/49 |

(Continued)

FOREIGN PATENT DOCUMENTS

| JP | 5205524 B2 | 6/2013 |
| JP | 5841189 B2 | 1/2016 |

(Continued)

OTHER PUBLICATIONS

Extended European Search Report received in corresponding European Application No. 19876440.9 dated Mar. 25, 2022.

(Continued)

*Primary Examiner* — Brian R Gordon
(74) *Attorney, Agent, or Firm* — MATTINGLY & MALUR, PC (57) ABSTRACT

Provided is a technique for increasing discriminating ability, preventing human error, and improving efficiency of discrimination in a discrimination operation for extracting a sample satisfying a specific condition from among a plurality of samples. A sample discrimination system according to the present disclosure is provided with a plurality of sample retaining devices for retaining samples, and a sample information query device for querying a sample retaining device that matches predetermined query information from among the plurality of sample retaining devices. The sample information query device has a query information input unit for inputting of predetermined query information, and a query information transmission unit for transmitting predetermined query information to the sample retaining devices. The sample retaining devices are each characterized by (Continued)

having a storage unit for storing sample information, a comparison unit for comparing predetermined query information and sample information, and a first display unit for outputting the result of comparison by the comparison unit.

16 Claims, 5 Drawing Sheets

(56) References Cited

U.S. PATENT DOCUMENTS

| | | | | |
|---|---|---|---|---|
| 11,073,525 | B2* | 7/2021 | Kaneko | G01N 35/00663 |
| 2004/0101912 | A1* | 5/2004 | Rubin | G01N 33/5079 |
| | | | | 382/128 |
| 2005/0207633 | A1* | 9/2005 | Arini | G01N 21/6452 |
| | | | | 382/133 |
| 2006/0265173 | A1* | 11/2006 | Mishima | G01N 35/00722 |
| | | | | 702/118 |
| 2008/0212866 | A1* | 9/2008 | Lett | G01N 21/6458 |
| | | | | 382/133 |
| 2008/0247914 | A1 | 10/2008 | Edens et al. | |
| 2009/0129990 | A1 | 5/2009 | Kokawa et al. | |
| 2010/0010746 | A1* | 1/2010 | Ariyoshi | G01N 35/00722 |
| | | | | 702/19 |
| 2011/0224574 | A1* | 9/2011 | Sadler | G01N 33/5091 |
| | | | | 600/562 |
| 2014/0370608 | A1 | 12/2014 | Gelbman et al. | |
| 2016/0281150 | A1* | 9/2016 | Rawlings | C12Q 1/6837 |
| 2017/0343475 | A1* | 11/2017 | Yamada | G01N 21/6428 |
| 2018/0003730 | A1* | 1/2018 | Watanabe | A61J 1/14 |
| 2018/0259440 | A1* | 9/2018 | Otsuka | G01N 15/14 |
| 2018/0267069 | A1* | 9/2018 | Katsumi | G16H 10/40 |
| 2019/0018031 | A1* | 1/2019 | Lee | G01N 35/00871 |
| 2019/0323057 | A1* | 10/2019 | Stern | B01L 3/5085 |
| 2019/0388889 | A1* | 12/2019 | Niemeyer | G01C 9/06 |
| 2020/0103346 | A1* | 4/2020 | Zhang | C12Q 1/6874 |

FOREIGN PATENT DOCUMENTS

| | | |
|---|---|---|
| JP | 6218753 B2 | 10/2017 |
| WO | 2010/056903 A1 | 5/2010 |

OTHER PUBLICATIONS

International Search Report of PCT/JP2019/040206 dated Dec. 24, 2019.

* cited by examiner

SAMPLE DISCRIMINATION SYSTEM AND SAMPLE AUTOMATIC PROCESSING APPARATUS USING SAME, AND SAMPLE DISCRIMINATION METHOD

TECHNICAL FIELD

The present disclosure relates to a sample discrimination system and a sample automatic processing apparatus using the same, and a sample discrimination method.

BACKGROUND ART

A sample automatic processing apparatus is configured so that a plurality of processing devices are connected to each other, a sample is conveyed between the processing devices, and a predetermined process is performed. In the sample automatic processing apparatus, multiple samples are simultaneously conveyed, and various processes different for each sample are performed. Thus, various results can be obtained by the processes. In a sample analysis using the sample automatic processing apparatus, a sample discrimination operation, for example, identifying individual samples or extracting a sample satisfying specific conditions from multiple samples is very important.

In the related art, a method of providing a barcode or a QR code (registered trademark) on the sample itself or a conveyor container for conveying the sample, or a method of discriminating the samples using an RFID or the like in a non-contact manner is adopted as a method of discriminating each sample to be conveyed in the sample automatic processing apparatus.

However, in the sample discrimination operation, it is required to improve the efficiency of the discrimination operation by an operator and prevent a human error. Thus, it is desirable to easily visually discriminate a sample satisfying a predetermined condition.

For example, PTL 1 discloses "a rack for retaining a plurality of sample containers for storing samples, in which the rack includes a main body including a plurality of receptacles, each receptacle is configured to retain one of the plurality of sample containers, the rack further includes a movable peg associated with each of the plurality of receptacles, each movable peg has a first position at which the movable peg is not seen, and a second position at which the movable peg is seen at least partially, in order to present, to an operator of an automatic clinical analyzer, whether an additional process is required after the sample associated with the receptacle firstly passes through the automatic clinical analyzer, each movable peg is driven by a motor configured to receive a signal generated by software and an algorithm from a controller/data processing module of the automatic clinical analyzer" (see claim 1 in PTL 1).

PTL 2 discloses a specimen rack storage unit that stores a plurality of sample racks for specimen conveyance, which are used in an automatic analyzer or a specimen pre-processing apparatus that inspects a specimen, after an analysis process or a pre-process is ended includes a contact terminal for supplying power to a color developing unit or a light emitting unit that performs display in accordance with a predetermined state of each specimen, which is detected when the analysis process or the pre-process is performed" (see claim 1 in PTL 2).

PTL 3 discloses "a method of displaying state information of a sample in an automated system that conveys the sample to be analyzed by an automatic analyzer by a carrier, in a control device of the automated system, that is provided in the carrier so that an operator can visually recognize a display surface that is electronically rewritable, the method including associating identification information of the sample with the carrier that receives the sample, receiving the state information regarding the received sample from the control device, and displaying the state information on the display surface by the associated carrier, in which the process of associating the identification information of the sample with the carrier includes discriminating the identification information of the sample from information of a barcode read from a sample container of the sample, and changing a state of the display surface of the associated carrier to distinguish the carrier from other carriers and notifying the operator that the sample is put into the carrier" (see claim 1 in PTL 3).

CITATION LIST

Patent Literature

PTL 1: Japanese Patent No. 5841189
PTL 2: Japanese Patent No. 5205524
PTL 3: Japanese Patent No. 6218753

SUMMARY OF INVENTION

Technical Problem

However, in the sample discrimination methods disclosed in PTLs 1 to 3, it is possible to classify a plurality of samples by many classification items, but, if the amount of information to be classified or information to be displayed increases, it is difficult to discriminate a desired sample.

Thus, the present disclosure is to provide a technique for increasing discriminating ability, preventing human error, and improving efficiency of discrimination in a discrimination operation for extracting a sample satisfying a specific condition from among a plurality of samples.

Solution to Problem

In order to solve the above problem, according to the present disclosure, a sample discrimination system includes a plurality of sample retaining devices that retain samples, and a sample information query device that transmits a query of the sample retaining device that matches predetermined query information among the plurality of sample retaining devices. The sample information query device includes a query information input unit configured to input the predetermined query information, and a query information transmission unit that transmits the predetermined query information to the sample retaining device. The sample retaining device includes a storage unit that stores sample information being information regarding the sample, a comparison unit that compares the predetermined query information transmitted from the sample information query device with the sample information stored in the storage unit, and a first display unit that outputs a comparison result by the comparison unit.

Further features relating to the present disclosure will become apparent from the description of the specification and the accompanying drawings. In addition, the aspects of the present disclosure are achieved and realized by elements, the combination of various elements, the detailed description below, and the aspects of the appended claims.

It should be understood that the description in the specification is merely a typical example and is not intended to limit the scope of the claims or the application example of the present disclosure in any sense.

Advantageous Effects of Invention

As described above, according to the configuration of the present disclosure, it is possible to increase discriminating ability, prevent human error, and improve efficiency of discrimination in a discrimination operation for extracting a sample satisfying a specific condition from among a plurality of samples.

Objects, configurations, and advantageous effects other than those described above will be clarified by the descriptions of the following embodiments.

DESCRIPTION OF EMBODIMENTS

A sample discrimination system and a sample discrimination method according to embodiments of the present disclosure will be described with reference to the drawings. In the present disclosure, the sample discrimination system is provided in a sample automatic processing apparatus that performs one or more processes on a plurality of samples. The sample automatic processing apparatus includes one or more processing devices.

First Embodiment

Figure 1:
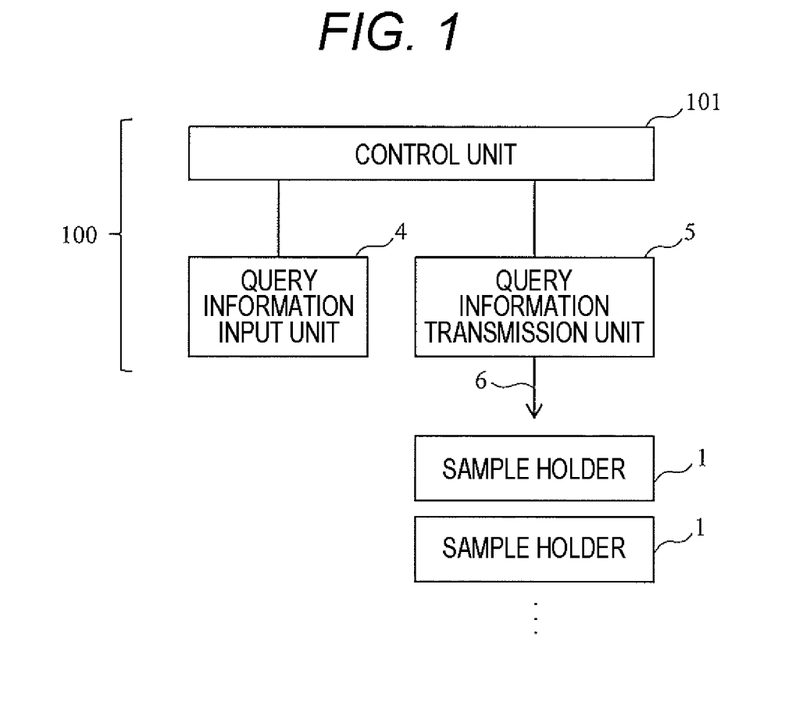
FIG. 1 is a block diagram illustrating a configuration of a sample discrimination system according to a first embodiment.

FIG. 1 is a block diagram illustrating a configuration of a sample discrimination system according to a first embodiment. The sample discrimination system in the present embodiment includes a sample information query device 100 and a plurality of sample holders 1 (sample retaining devices).

The sample information query device 100 is means for discriminating a sample holder 1 that matches predetermined query information 6, and includes a query information input unit 4, a query information transmission unit 5, and a control unit 101.

The query information input unit 4 is means for setting the query information 6 which is information intended to be inquired among pieces of information regarding samples retained in the plurality of sample holders 1. The query information 6 may be appropriately input, for example, by an operator, or information obtained during each process by the sample automatic processing apparatus (not illustrated) may be used as the query information 6. The query information 6 is, for example, information such as the name of the sample, information regarding the executed process, a result of a predetermined process, and the date and time when the sample is prepared.

The query information transmission unit 5 transmits the query information 6 input from the query information input unit 4 to the sample holder 1.

Figure 2:
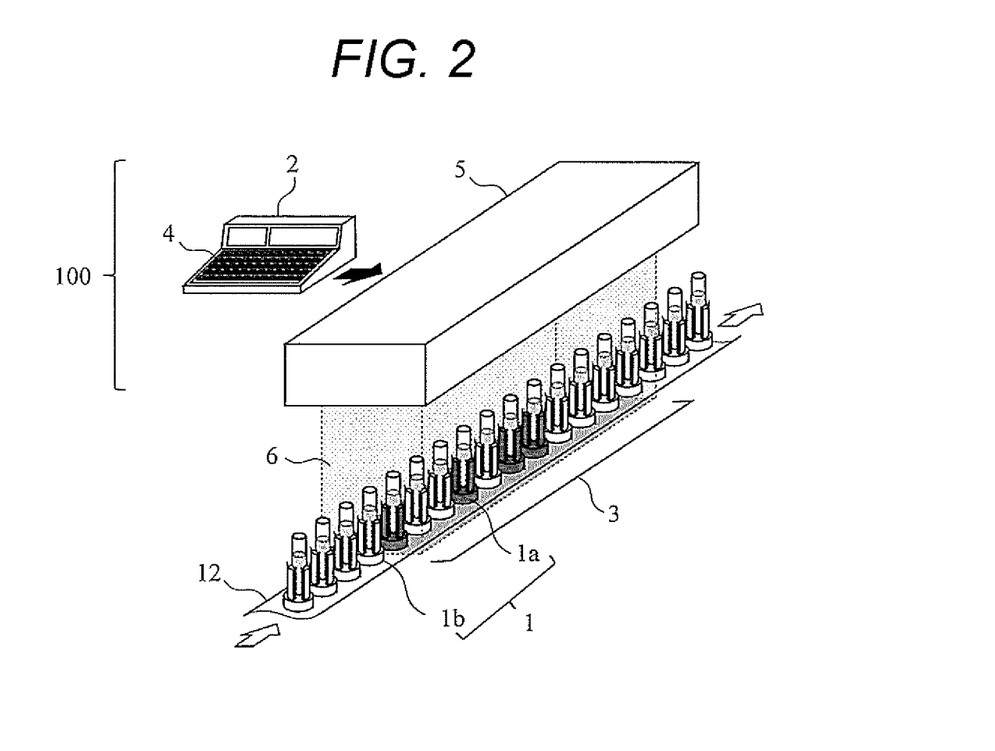
FIG. 2 is a schematic diagram illustrating a hardware configuration of the sample discrimination system according to the first embodiment.

FIG. 2 is a schematic diagram illustrating a hardware configuration of the sample discrimination system according to the first embodiment. As illustrated in FIG. 2, the sample holder 1 is two-dimensionally placed on a conveyor belt 12 and conveyed in a sample automatic analyzer. Note that, the sample holder 1 may be placed on another support unit on which a plurality of sample holders 1 can be placed, such as a plate or a rack, for example.

As illustrated in FIG. 2, the sample information query device 100 includes an input device 2 and the query information transmission unit 5. As the query information input unit 4, an input device such as a keyboard or a mouse of the input device 2 can be used. The input device 2 is, for example, a personal computer or the like installed around the query information transmission unit 5. The input device is connected to the query information transmission unit 5 in a wired or wireless manner or the like to output the query information 6 input from the query information input unit 4 to the query information transmission unit 5.

Although not illustrated in FIG. 2, the control unit 101 is a processor, a computer, or the like mounted in the input device 2. The control unit 101 outputs the query information 6 input from the query information input unit 4 to the query information transmission unit 5.

The query information transmission unit 5 is disposed, for example, above the sample holder 1, and transmits the query information 6 to a sample holder 1a located in a predetermined query region 3. The query region 3 is a region having any area, for example, a region visible to an operator, a predetermined section on the conveyor belt 12 on which the sample holder 1 is placed, and the like. The query information transmission unit 5 does not transmit the query information 6 to a sample holder 1b located outside the query region 3.

As the query information transmission unit 5, for example, an information transmission device, an irradiation device, or the like capable of transmitting the query information 6 by light, radio waves, magnetism, or the like can be used. Among the devices, the use of light has advantages as follows. Firstly, since light has high directivity and is easily shielded, it is possible to easily prevent the leakage of the query information 6 to the outside of the query region 3, and to suppress an erroneous operation of the sample holder 1b outside the query region 3.

In addition, the query region 3 can be visually discriminated by transmitting the query information 6 by visible light. Furthermore, it is possible to retain and transmit a large amount of information by using wavelength patterns and light emission patterns in a plurality of bands including visible light and invisible light. By using a light emission pattern having a frequency that is as high as cannot be visually recognized, it is possible to easily transmit a large amount of information and suppress flicker caused by mixing with visible light emitted to the query region 3.

In the present embodiment, in the sample discrimination system, the query region 3 is not limited to one place. A configuration in which a plurality of query regions 3 are provided, and different pieces of the query information 6 are transmitted may be made. In this case, the query information 6 is preferably transmitted to the adjacent query region 3 by irradiation light of a different color. Thus, it is possible to visually discriminate each query region 3.

A plurality of query regions 3 to which different pieces of query information 6 are transmitted are required not to overlap each other. Further, it is necessary to prevent simultaneous transmission of a plurality of pieces of different query information 6 to one sample holder 1a. This is because, if different pieces of query information 6 are simultaneously transmitted to one sample holder 1a, it becomes unclear which query information 6 the sample holder 1a may process.

On the other hand, unlike radio waves, light has high directivity and almost no possibility of interference occurring. Thus, by transmitting the query information 6 by light, it is possible to arrange the query regions 3 to which different pieces of query information 6 are transmitted, to be close to each other. In a case where the different query regions 3 overlap each other, it is possible to easily find the overlapped portion because rays of irradiation light overlap each other.

Further, the light is not influenced by an electromagnetic wave generated by an actuator or the like used in the sample automatic processing apparatus. Thus, it is easy to improve the reliability of communication. In addition, it is possible to transmit the query information 6 with a relatively small amount of energy by using the light.

The sample information query device 100 may include a query region clarifying unit capable of discriminating where the query region 3 to which the query information 6 is transmitted is. As described above, the query region clarifying unit may be, for example, an irradiation device that is integrated with the query information transmission unit 5 to emit visible light from above the query region 3 or an irradiation device that is disposed below or inside the conveyor belt 12 as a member separate from the query information transmission unit 5 and emits visible light from below the query region 3. The position at which the query region clarifying unit is disposed, and a method of clarifying the query region 3 are not limited to the above-described arrangement and the clarifying method as long as the operator can visually discriminate the query region 3. For example, a configuration in which an elevating device is provided below the sample holder 1 to raise only the sample holder 1a located in the query region 3 may be made.

Note that, the position of the query information transmission unit 5 is not limited to a position above the sample holder 1a as long as the query information 6 can be transmitted to the sample holder 1a located in the query region 3. For example, in a case where the conveyor belt 12 on which the sample holder 1 is placed is formed of a material enabling light, radio waves, magnetism, and the like to pass therethrough, the query information 6 may be transmitted from below the conveyor belt 12.

Figure 3:
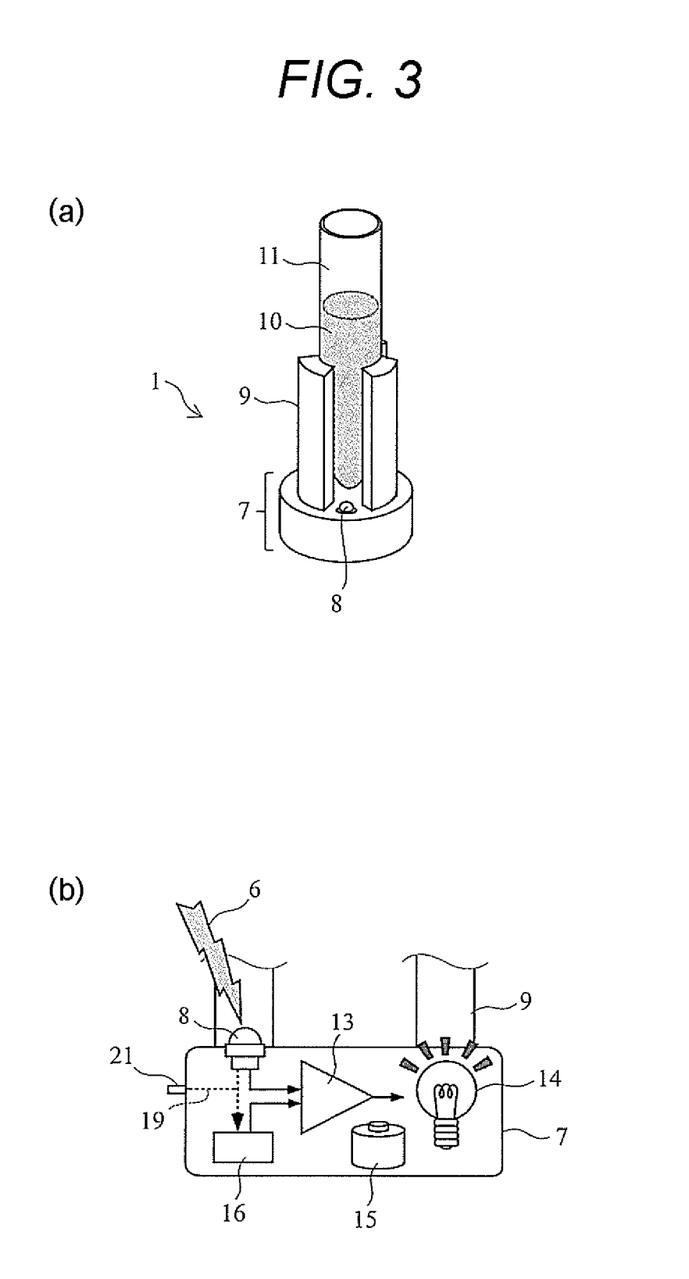
FIG. 3 is a schematic diagram illustrating a configuration of a sample holder.

FIG. 3 is a schematic diagram illustrating a configuration (a) of the sample holder 1 and an internal configuration (b) of a bottom 7. As illustrated in FIGS. 3(a) and 3(b), the sample holder 1 includes the bottom 7 and a guide 9 that support a test tube 11 that stores the sample 10. A receiving unit 8, a comparison unit 13, a comparison result display unit (first display unit) 14, a power supply 15, a storage unit 16, and an information storage route 19 are built in the bottom 7.

As illustrated in FIG. 3(b), the receiving unit 8 is disposed so that a portion of the receiving unit 8 is exposed from the upper surface of the bottom 7, and is configured to be able to receive the query information 6. As the receiving unit 8, for example, a sensor or a receiver capable of receiving light, radio waves, or Magnetism can be used.

The storage unit 16 is configured by a memory or the like that stores sample information which is information regarding the sample 10. The sample information is, for example, data generated when the sample 10 is prepared or analyzed. For example, the sample information is input from the outside through the receiving unit 8 and is stored in the storage unit 16 via the information storage route 19. The sample information may be input to the receiving unit 8 by light, or by an RFID, a vibration pattern, or the like and be stored in the storage unit 16 in a similar manner to the above description. In addition, a terminal 21 connected to the sample automatic processing apparatus may be provided on the bottom 7 of the sample holder 1, and the sample information may be input from the sample automatic processing apparatus via the terminal 21, and be stored in the storage unit 16 via the information storage route 19.

The comparison unit 13 is configured by, for example, a comparator or the like. If the query information 6 is transmitted from the query information transmission unit 5 to the receiving unit 8, the comparison unit 13 compares the query information 6 with the sample information stored in the storage unit 16. For example, it is determined whether the query information 6 and the sample information coincide with each other. The comparison unit 13 outputs a comparison result to the comparison result display unit 14. The comparison unit 13 may output the comparison result to the comparison result display unit 14 only in a case where the query information 6 and the sample information coincide with each other, or may output the comparison result to the comparison result display unit 14 regardless of whether or not the query information and the sample information coincide with each other.

The comparison result display unit 14 is configured to perform display the comparison result to be visually enabled to be discriminated from the outside. The comparison result display unit 14 may display the comparison result only when the query information 6 and the sample information coincide with each other, or may change the display in accordance with the comparison result of coincidence or not-coincidence. Further, the display may be changed in accordance with the received query information 6. As the comparison result display unit 14, for example, a lamp including a light emitting element, a display device such as a display, or the like can be used. Furthermore, the comparison result may be reported to the operator by sound.

In the example illustrated in FIG. 2, a lamp including a light emitting element such as an LED element is used as the comparison result display unit 14, and the comparison result is displayed by illuminating the entire sample holder 1 by light emission. In this case, the bottom 7 and the guide 9 of the sample holder 1 are preferably formed of a transparent or translucent resin or the like so that light can be transmitted therethrough. In a case where the comparison result display unit 14 displays the comparison result by light emission, for example, light emission is performed only when the query information 6 and the sample information coincide with each other. In this manner, it is possible to visually discriminate the sample holder 1 that matches the query information 6. FIG. 2 illustrates a state in which light is emitted from only the sample holder 1a that matches the query information 6 is emitting light.

In a case where visible light is emitted by the query information transmission unit 5, it is possible to easily discriminate the sample holder 1 that matches the query information 6 by setting the color of the irradiation light and the light emission color of the comparison result display unit 14 to be different from each other. By selecting light having a color tone different from the light emitted to the query region 3, for example, the opposite color, as the light emission color of the comparison result display unit 14, it is easy to discriminate the comparison result even among rays of the light emitted to the query region 3. Further, by using an LED element or the like as a light source of the comparison result display unit 14, it is possible to suppress the energy required for displaying the comparison result to a small value. Further, even though the sample holder 1 is small, it is easy to discriminate the comparison result by shining the entire sample holder 1.

In addition, the comparison result display unit 14 may have a configuration of displaying the comparison result with, for example, a circle mark and a cross mark, or a configuration of displaying the comparison result by setting a flag or turning the flag down.

The power supply 15 supplies electric power for operating the receiving unit 8, the comparison unit 13, the comparison result display unit 14, and the storage unit 16. As the power supply 15, for example, a commonly used battery or a solar cell can be used. In a case where the query information 6 is transmitted to the sample holder 1 by light, it is preferable that the comparison result display unit 14 operates only while the light is being received in order to prevent an erroneous operation. Thus, by using the solar cell as the power supply 15, it is possible to photoelectrically convert the light energy of the query information 6 to secure sufficient electric power, and there is no concern that the battery will run out. In addition, by disposing the solar cell at a position at which the solar cell is able to receive light, it is not necessary to incorporate the battery. By incorporating a secondary battery or the like in addition to the solar cell, it is possible to use power generated by the light received during a period other than a period when the light of the query information 6 is being received. In order to secure the required power, it is effective to increase the area of the solar cell and to intensify the irradiation light of the query information 6 to a sufficient brightness.

Since the solar cell is basically a photoelectric conversion element, the solar cell can also be used as the receiving unit 8. If the sample holder 1 is operated by using the electric power energy obtained by the receiving unit 8 which is a photoelectric conversion element, it is not necessary to provide the power supply 15.

In the example of FIG. 3, it is assumed that the sample 10 is stored in the test tube 11, but there are various forms of the container for storing the sample 10, and the sample holder 1 may be required to have a shape corresponding to the form. As described above, the display method of causing light to be emitted from the entire sample holder 1 by the internal light emission by the comparison result display unit 14 can correspond to a sample holder 1 having a relatively wide form.

Note that, it is possible to set the query information 6 from a control system (not illustrated) that controls the entirety of the sample automatic processing apparatus, and to use the control system of the sample automatic processing apparatus as the control unit 101. That is, the query information input unit 4 and the control unit 101 may be provided in the sample automatic processing apparatus instead of the input device 2. By transmitting information obtained during each process by the sample automatic processing apparatus, as the query information 6 to the control system of the sample automatic processing apparatus, and linking the control system of the sample automatic processing apparatus with the query information 6, it is possible to reduce the input error of the query information 6 by the operator and to simplify the device configuration.

Figure 4:
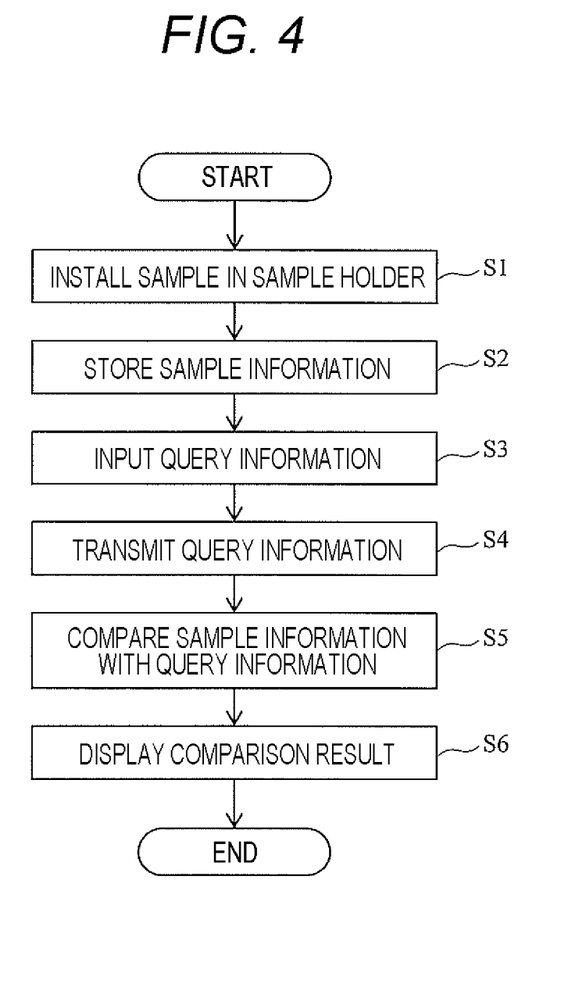
FIG. 4 is a flowchart illustrating a sample discrimination method according to the first embodiment.

Next, a sample discrimination method by the sample discrimination system according to the present embodiment will be described with reference to FIG. 4. In the sample discrimination method described below, the sample information query device 100 and various processing devices (not illustrated) included in the sample automatic processing apparatus are controlled by the control unit 101.

Firstly, in Step S1, if the operator installs a sample 10 in a sample holder 1 and starts a process in the sample automatic processing apparatus, the control unit 101 drives various processing devices, and the various processing devices execute a predetermined process on the sample 10 retained by each sample holder 1.

In Step S2, the control unit 101 receives sample information output from each processing device and transmits the sample information to the sample holder 1. The sample holder 1 receives the sample information by, for example, the receiving unit 8, and the storage unit 16 stores the sample information.

In Step S3, the operator inputs query information 6 from the query information input unit 4 of the input device 2. The query information input unit 4 outputs the input query information 6 to the control unit 101. The control unit 101 outputs the input query information 6 to the query information transmission unit 5. At this time, the control unit 101 may generate a transmission pattern of the query information 6 by the query information transmission unit 5, based on the query information 6 from the query information input unit 4.

In Step S4, the query information transmission unit 5 receives the query information 6 from the control unit 101 and transmits the query information 6 to a sample holder 1*a* located in a predetermined query region 3.

In Step S5, the receiving unit 8 of the sample holder 1*a* receives the query information 6 and outputs the query information to the comparison unit 13. The comparison unit compares the query information 6 received from the receiving unit 8 with the sample information stored in the storage unit 16. The comparison unit 13 outputs a comparison result to the comparison result display unit 14.

In Step S6, the comparison result display unit 14 receives the comparison result from the comparison unit 13. In a case where the comparison result indicates that the sample information stored in the storage unit 16 matches the query information 6, the comparison result display unit displays or reports the comparison result by light emission. Thus, the operator can easily visually discriminate that the sample holder 1*a* from which light is emitted matches the query information 6.

Note that, in the sample discrimination method in the present embodiment, the sample information query device 100 and various processing devices included in the sample automatic processing apparatus are controlled by the control unit 101. The control system (not illustrated) of the sample automatic processing apparatus may control the various processing devices and control the sample information query device 100.

As described above, the sample discrimination system according to the present embodiment has a configuration in which the query information 6 is transmitted only to the sample holder 1*a* located in the predetermined query region 3, and the comparison result display unit 14 of the sample holder 1*a* performs display so that conformity or nonconformity with the query information 6 can be visually discriminated. As described above, since the display of conformity or nonconformity with the query information 6 is simple, it is possible to suppress an artificial discrimination error. Thus, in the discrimination operation of extracting a sample that matches a specific condition from a plurality of samples, it is possible to increase discriminating ability, improve efficiency of the discrimination operation, and prevent a human error.

Second Embodiment

Figure 5:
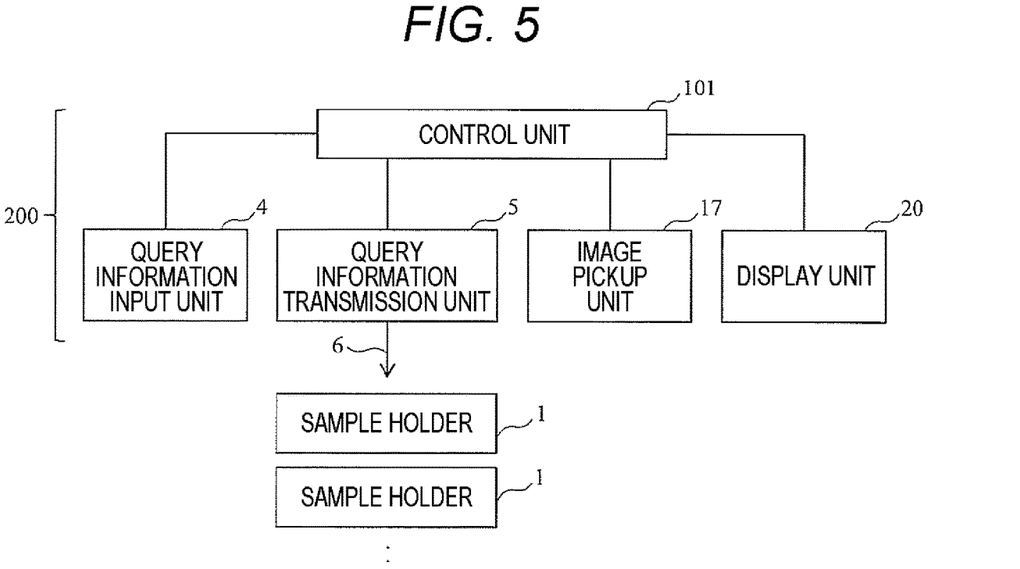
FIG. 5 is a block diagram illustrating a configuration of a sample discrimination system according to a second embodiment.

A sample discrimination system according to a second embodiment will be described with reference to FIGS. 5 to 7. FIG. 5 is a block diagram illustrating a configuration of the sample discrimination system according to the present embodiment. As illustrated in FIG. 5, the sample discrimination system according to the present embodiment is different from that in the first embodiment in that a sample information query device 200 includes an image pickup unit (comparison result detection unit) 17 and a display unit (second display unit) 20.

Figure 6:
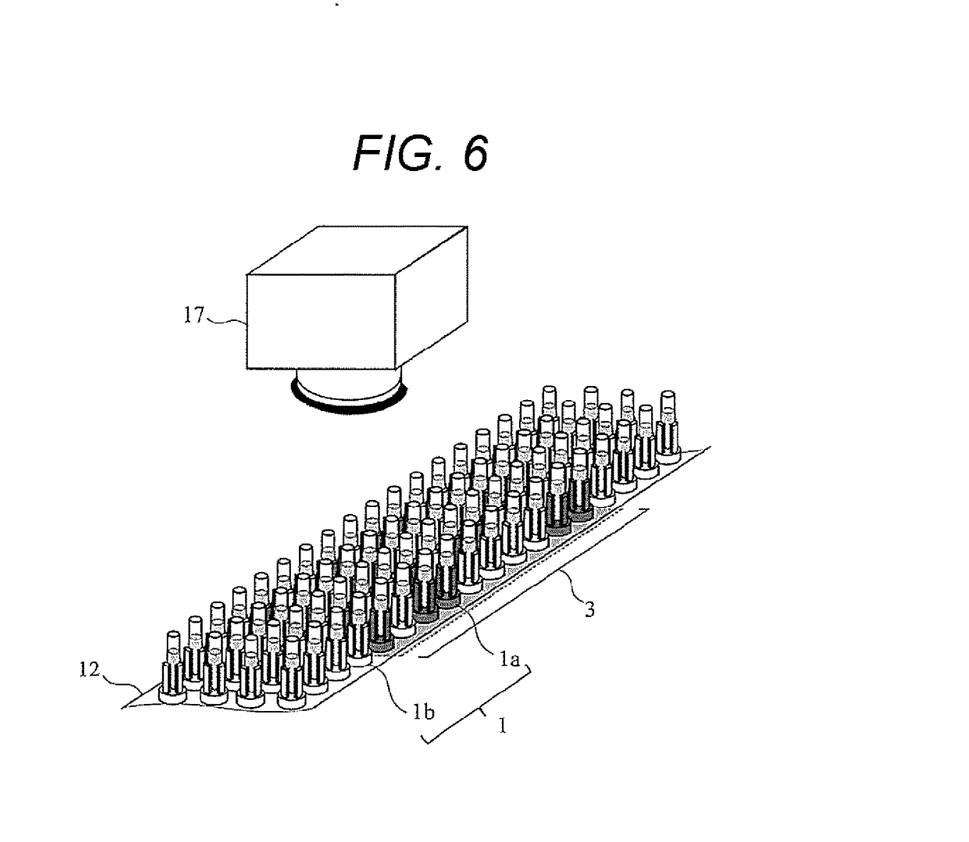
FIG. 6 is a schematic diagram illustrating a hardware configuration of the sample discrimination system according to the second embodiment.
Figure 7:
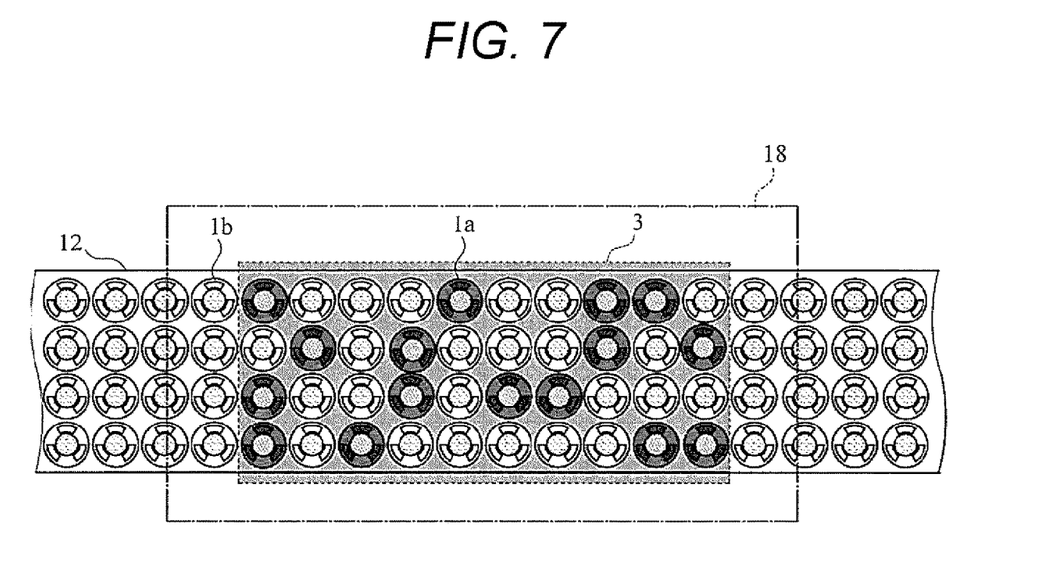
FIG. 7 is a schematic diagram illustrating an example of an image pickup region detected by an image pickup unit.

FIG. 6 is a schematic diagram illustrating a hardware configuration of the sample discrimination system according to the present embodiment. FIG. 7 is a schematic diagram illustrating an example of an image pickup region 18 detected by the image pickup unit 17. Note that, in FIG. 6, the display unit 20 is not illustrated.

As illustrated in FIGS. 6 and 7, the query region 3 is, for example, a region including sample holders 1a of 10 pieces×4 rows, but the query region is not limited to this. As the image pickup unit 17, for example, an optical camera such as a CCD camera, a CMOS sensor, or the like can be used. As the display unit 20, for example, a display device such as a display device can be used.

The image pickup unit 17 is disposed above the query region 3, picks up an image of an image pickup region 18 including the query region 3, and detects the comparison result of the comparison unit 13. The image (detection result) picked up by the image pickup unit 17 is displayed on the display unit 20. The image pickup region 18 preferably has a wider range than the query region 3. Thus, the query region 3 illuminated by the light of the query information 6 can be confirmed at a time, and the operator easily discriminates which position of the sample holder 1a in the query region 3 matches the query information 6. As illustrated in FIG. 7, the color of the sample holder 1a that matches the query information 6 among the sample holders 1a located in the query region 3 is different, and thus the operator can determine which sample holder 1a emits light, at a glance.

The image picked up by the image pickup unit 17 may be transmitted to the control unit 101. The control unit 101 may calculate position information of the sample holder 1a in the query region 3, and determine a position of which the sample holder 1a matches the query information 6. In this case, the control unit 101 may display the position information of the sample holder 1a that matches the query information 6, on the display unit 20.

The display unit 20 may display information regarding the comparison result to be superimposed on the image picked up by the image pickup unit 17. For the information regarding the comparison result, for example, a cross mark can be displayed on the sample holder 1a that is located in the query region 3 but does not match the query information 6, or a mask can be displayed for the sample holder 1b located outside the query region 3.

Note that, although the query information input unit and the query information transmission unit 5 are not illustrated in FIG. 6, the query information transmission unit 5 may be disposed below the conveyor belt 12. In this case, in a case where light is used to transmit the query information 6, the member of the conveyor belt 12, which is located below the sample holder 1 is made of a material that allows light, radio waves, magnetic fields, and the like to be transmitted therethrough, and the receiving unit 8 of the sample holder 1 is disposed at a position at which the query information 6 transmitted from below can be detected.

As described above, the sample discrimination system according to the present embodiment has a configuration of detecting the comparison result between the sample information stored in the sample holder 1 and the query information 6 and displaying the comparison result on the display unit 20. Thus, it becomes easier for the operator to visually discriminate which sample holder 1 matches the query information 6. Thus, in the discrimination operation of extracting a sample that matches a specific condition from a plurality of samples, it is possible to increase discriminating ability, improve efficiency of the discrimination operation, and prevent a human error.

The present disclosure is not limited to the examples described above, and includes various modification examples. For example, the above-described examples are described in detail in order to explain the present disclosure in an easy-to-understand manner, and it is not necessary to include all the configurations described above. In addition, a portion of one example can be replaced with the configuration of another example. Further, it is also possible to add the configuration of one example to the configuration of another example. In addition, it is also possible to add, delete, or replace a portion of the configuration of another example with respect to a portion of the configuration of each example.

REFERENCE SIGNS LIST 100,200 sample information query device
1 sample holder
2 input device
3 query region
4 query information input unit
5 query information transmission unit
6 query information
7 bottom
8 receiving unit
9 guide
10 sample
11 test tube
12 conveyor belt
13 comparison unit
14 comparison result display unit
15 power supply
16 storage unit
17 image pickup unit
18 image pickup region
19 information storage route
20 display unit
21 terminal

The invention claimed is:
1. A sample discrimination system comprising:
a plurality of sample retaining devices configured to retain samples;
a computer; and a query information transmission unit, coupled to the computer, configured to transmit a query containing predetermined query information to the plurality of sample retaining devices, wherein the computer is configured to receive an input of the predetermined query information, wherein each of the plurality of sample retaining devices includes:
- a storage storing sample information of a sample among the samples,
- a comparison unit, coupled to the storage unit, configured to compare the predetermined query information after being transmitted from the query information transmission unit with the sample information stored in the storage unit, and
- a first display unit, coupled to the comparison unit, configured to display an indication of a comparison result of the comparison unit.

2. The sample discrimination system according to claim 1, wherein the query information transmission unit is configured to transmit the predetermined query information by light.

3. The sample discrimination system according to claim 1, wherein the query information transmission unit is configured to transmit the predetermined query information to one or more sample retaining devices among the plurality of sample retaining devices located in a predetermined query region and to enable the predetermined query region to be visually identifiable, the predetermined query region being a region between the query information transmission unit and the plurality of sample retaining devices.

4. The sample discrimination system according to claim 3, wherein the query information transmission unit is configured to emit the predetermined query region with visible light.

5. The sample discrimination system according to claim 1, wherein the plurality of sample retaining devices further include a photoelectric conversion element.

6. The sample discrimination system according to claim 5, wherein the photoelectric conversion element is a receiving unit configured to receive the predetermined query information.

7. The sample discrimination system according to claim 1, wherein the comparison unit is configured to determine whether the sample information stored in the storage unit corresponds with the predetermined query information transmitted by the query information transmission unit, and wherein the first display unit is configured to indicate whether the sample information stored in the storage unit corresponds or does not correspond with the predetermined query information.

8. The sample discrimination system according to claim 1, further comprising:
a comparison result detection unit configured to detect the display of the indication of the comparison result of a sample retaining device among the plurality of sample retaining devices, wherein the computer is configured to acquire position information of the plurality of sample retaining devices based on a detection result by the comparison result detection unit.

9. The sample discrimination system according to claim 8, wherein the comparison result detection unit is an optical camera.

10. The sample discrimination system according to claim 8,
wherein the computer further includes a second display unit configured to display the detection result,
wherein the computer is configured to display, on the second display unit, information about the comparison result to be superimposed on the detection result, based on the detection result and the position information.

11. A sample discrimination method comprising:
preparing a plurality of sample retaining devices that retain respective samples, each of the plurality of sample retaining devices storing sample information of a respective sample among the samples in a respective storage unit;

receiving, by a computer, predetermined query information, and preparing, by the computer, a query for a sample retaining device among the plurality of sample retaining devices corresponding to the predetermined query information;

transmitting a query containing predetermined query information to the plurality of sample retaining devices, by a query information transmission unit;

receiving the predetermined query information and comparing the predetermined query information with the sample information, by a comparison unit of each of the plurality of sample retaining devices; and outputting an indication of a result of the comparison, by a first display unit in each of the plurality of sample retaining devices.

12. The sample discrimination method according to claim 11,
wherein in the step of transmitting the predetermined query information, the query information transmission unit transmits the predetermined query information by light.

13. The sample discrimination method according to claim 11,
wherein in the step of transmitting the predetermined query information, the query information transmission unit transmits the predetermined query information to one or more sample retaining devices, among the plurality of sample retaining devices, located in a predetermined query region and enables the predetermined query region to be visually identifiable, the predetermined query region being a region between the query information transmission unit and the plurality of sample retaining devices.

14. The sample discrimination method according to claim 11,
wherein in the step of comparing the predetermined query information with the sample information, the comparison unit of each of the plurality of sample retaining devices determines whether the stored sample information corresponds with the received predetermined query information, and in the step of outputting the result of the comparison, the first display unit of each of the plurality of sample retaining devices indicates whether the sample information stored in the storage unit corresponds with the predetermined query information.

15. The sample discrimination method according to claim 11, further comprising:
a step of detecting the result of the comparison by a comparison result detection unit; and
a step of acquiring position information of the plurality of sample retaining devices device based on a result of the detecting.

16. The sample discrimination method according to claim 15, further comprising:
 a step of receiving the result of the detection by the comparison result detection unit and displaying information regarding the result of the comparison to be superimposed on the result of the detection, based on the result of the detection and the position information, by a second display unit configured to be able to display the result of the detection by the comparison result detection unit.

* * * * *